(12) United States Patent
Oka et al.

(10) Patent No.: US 6,194,225 B1
(45) Date of Patent: Feb. 27, 2001

(54) IMMUNOCHROMATOGRAPHY-ASSISTED DEVICE

(75) Inventors: Miwa Oka, Uji; Nobuyuki Shigetou, Hirakata; Jinsei Miyazaki, Higashiosaka, all of (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/154,025

(22) Filed: Sep. 16, 1998

(30) Foreign Application Priority Data

| Sep. 18, 1997 | (JP) | 9-253072 |
| Sep. 18, 1997 | (JP) | 9-253074 |

(51) Int. Cl.$^7$ .................................................. G01N 33/533
(52) U.S. Cl. .......................... 436/518; 435/7.1; 435/7.5; 435/7.92; 435/970; 436/501; 436/514; 436/523; 436/536; 436/532; 436/169; 436/810; 436/823; 422/56; 422/57; 422/58; 422/60
(58) Field of Search .......................... 435/7.1, 7.5, 7.92, 435/7.9; 436/523, 514, 536, 518, 501, 532, 169; 422/56, 57, 58, 60

(56) References Cited

U.S. PATENT DOCUMENTS

| 4,868,106 | * | 9/1989 | Ito et al. . | |
| 5,178,831 | * | 1/1993 | Sakota et al. | 422/56 |
| 5,356,782 | * | 10/1994 | Moorman et al. | 435/7.9 |
| 5,384,264 | | 1/1995 | Chen et al. . | |
| 5,424,220 | | 6/1995 | Goerlach-Graw et al. . | |
| 5,602,040 | | 2/1997 | May et al. . | |
| 5,770,458 | * | 6/1998 | Klimov et al. . | |
| 5,922,618 | * | 7/1999 | Shigetou et al. | 436/532 |

FOREIGN PATENT DOCUMENTS

| 250137 | | 12/1987 | (EP) . |
| 505636 | | 9/1992 | (EP) . |
| 653635 | * | 5/1995 | (EP) . |
| 05052836 | | 3/1993 | (JP) . |
| 09184840 | | 7/1997 | (JP) . |

* cited by examiner

Primary Examiner—Christopher L. Chin
Assistant Examiner—Bao-Thuy L. Nguyen
(74) Attorney, Agent, or Firm—McDermott, Will & Emery

(57) ABSTRACT

An immunochromatography-assisted device is disclosed which facilitates accurate and rapid detection of an antigen contained in a fluid sample and from which background coloring and blank coloring possibly causing a malfunction at detection are successfully eliminated. The immunochromatography-assisted device comprises a porous carrier having an additive-impregnated part between a sample introducing part and a determining part, the additive-impregnated part carrying at least one selected from the group consisting of a surfactant, a water-soluble ammonium salt and a pH buffer such that it dissolves in a sample introduced into the carrier in order to move with the movement of the sample through the carrier. The porous carrier also has a labelled part segmented into plural zones.

17 Claims, 12 Drawing Sheets

IMMUNOCHROMATOGRAPHY-ASSISTED DEVICE

BACKGROUND OF THE INVENTION

The present invention relates to an extracorporeal diagnostic drug or a portable diagnostic device for detecting microorganisms in water and a trace amount of markers in the humor. More specifically, the present invention is intended to improve the performance of an immunochromatography-assisted device which facilitates simple and rapid measurements of such substances at small-scale clinics with no installation of analytical equipment and by the subjects studied.

Extracorporeal diagnostic drugs for detecting a trace amount of markers in the body fluids such as urine, sweat and blood have recognized importance as the major aids for clinical diagnosis and home care medicine. Immunochromatography is a basic technology for extracorporeal diagnostic drugs which best use specific reaction of an antibody. Among them, the most typical and widely applied immunochromatography-assisted device in the market as a general medicine is pregnancy testing drug. When pregnant, women secret human chorionic gonadotropin (hCG) from the placenta, which is later excreted in urine. Upon introduction of a female urine sample, a pregnancy tester determines whether the urine is positive or negative for pregnancy usually within 3 minutes or so, facilitating easy evaluation of pregnancy by any non-skilled ordinary person. A representative structure of such immunochromatography-assisted device is disclosed in the U.S. Pat. No. 5,602,040, for example.

In the following, the structure and operation of a most simple immunochromatography-assisted device will be described, taking the pregnancy tester as an example. FIG. 1 illustrates the structure of a porous carrier for use in a typical immunochromatography-assisted device. The most widely used porous carrier is a sheet of nitrocellulose because the material readily allows fixation of an antibody. However, if the porous carrier 1 is formed with this material entirely, the flow rate of a sample reduces prominently. Therefore, it is preferable for the carrier to be formed with nitrocellulose only for a determining part and with a glass filter which allows a sample to flow more rapidly for the rest. A sample introducing part 2 located at one end of the carrier is made of a porous carrier such as glass filter that inherently absorbs a sample rapidly but is weak in retaining the sample, thus permitting a rapid and smooth passage of the sample toward a reaction-related part. If the porous carrier 1 is to be accommodated in a hollow case, the sample introducing part 2 is formed relatively long so as to partially expose it from the case to allow direct introduction of a urine sample into the sample introducing part 2. Alternatively, if the entire sample introducing part 2 is to be accommodated in the case, the case should have an aperture through which a sample is introduced into the sample introducing part.

A labelled part 3 is formed by impregnating a glass filter with an aqueous solution of an anti-hCG antibody which is adsorbed on colloidal gold or colored latex, followed by freezing and drying it. A determining part 4 is produced by dropping an aqueous solution of another antibody on a nitrocellulose sheet in an arbitrary shape, followed by drying and rinsing it. The very strong non-specific adsorption property of nitrocellulose ensures tight adhesion of the antibody to the nitrocellulose sheet. After fixation of the antibody, the nitrocellulose sheet may be surface-treated with bovine serum albumin (hereinafter abbreviated to "BSA"), for example, in order to prevent coloring of the background due to the non-specific adsorption property of nitrocellulose during antigen-antibody reaction for detection. This surface treatment is called blocking. A fluid absorbing part 5 located at the other end of the porous carrier is formed with a material such as glass filter which is excellent in fluid absorption and fluid absorbing capacity, for the purpose of rapid absorption of excess sample.

As a sample, female urine is introduced into the sample introducing part 2 in an amount as determined based on the shape of the immunochromatography-assisted device (normally 0.1 to 2 ml). The sample passes through the determining part 4 via the labelled part 3 toward the fluid absorbing part 5. When the sample passes around the labelled part 3, the labelled antibody which is carried on the labelled part 3 dissolves in water in the sample and is transferred toward the determining part 4 together with the sample. Subsequently, the labelled antibody dissolved in water arrives at the determining part 4. At that time, if the urine is positive for pregnancy, the labelled antibody reacts with the fixed antibody present at the determining part 4 via an antigen in the urine sample based on the specific antigen-antibody binding reaction, which causes the determining part 4 to be colored, If negative, such reaction would not occur and the labelled antibody uneventfully passes the determining part 4 to be absorbed in the fluid absorbing part. In this way, the presence or absence of an antigen in an aqueous sample solution can be determined.

In such immunochromatography-assisted device as described above, coloring of the part other than the antibody in a fixed phase present at the determining part (background coloring) and coloring of the antibody in the fixed phase in the absence of an analyte (blank coloring) reduce the S/N ratio during detection and become a factor for causing a malfunction. Background coloring is caused by a hydrophobic bond between a visualized antibody in a mobile phase and the porous carrier. On the other hand, blank coloring is caused by electrical interaction between the negative-charged antibody in the mobile phase and the positive-charged antibody in the fixed phase.

Normal samples for use in detection are free of such substance as surfactant, pH buffer or the like that offsets a hydrophobic bond and electrical interaction. Therefore, the conventional immunochromatography-assisted device has drawbacks of development of not a little background coloring and occasional development of blank coloring. These drawbacks are particularly prominent when the antibody in the mobile phase is visualized with an organic dye.

Such immunochromatography-assisted device can be improved for its detectability by increasing the amount or concentration of the labelled antibody to be carried on the labelled part. However, this method disadvantageously increases the time until visual confirmation of background decoloring by sufficient depletion of the labelled antibody. In other words, an improvement in detectability contradicts a reduction in reaction time. If the antigen contained in a sample is over excess, the overall antibody in the mobile phase has to participate in antigen-antibody reaction, causing depletion of the mobile phase antibody at the determining part, which results in a malfunction of the device such that the amount of antigen is small seemingly. This is why a dynamic range in which reaction takes place essentially is preset in immunochromatography. The dynamic range for developing reaction is generally 50 to 100,000 IU/L with respect to the pregnancy tester.

Moreover, if an immunochromatography-assisted device is configured so as to ensure movement of a sample toward the determining part via the labelled part, hCG reacts with the labelled antibody before it reacts with the fixed antibody. Such structure is disadvantageous in detecting a low concentration of antigen as an analyte.

BRIEF SUMMARY OF THE INVENTION

In view of the above-mentioned drawbacks of the prior art device, the object of the present invention is to provide an immunochromatography-assisted device facilitating accurate and rapid detection of an antigen contained in a liquid sample by eliminating coloring of the background and blank coloring which may cause a malfunction during detection.

Another object of the present invention is to provide an epoch-making immunochromatography-assisted device for realizing improved detectability and reduced reaction time at the same time, and further for achieving an extended dynamic range for reaction.

In order to solve the above-mentioned problems, the present invention provides an immunochromatography-assisted device comprising a porous carrier having an impregnated part with an additive located between a sample introducing part and a determining part of the porous carrier, wherein the additive-impregnated part carries thereon at least one selected from the group consisting of a surfactant, a water-soluble ammonium salt and a pH buffer such that it dissolves in a sample introduced into the carrier in order to move with the movement of the sample through the carrier.

The present invention also provides an immunochromatography device, wherein the labelled part is segmented into plural zones.

The present invention provides a further immunochromatography-assisted device comprising a test strip composed of a porous carrier which has a labelled part containing one of two antibodies and a determining part containing the other of the two, the labelled part and the determining part being arranged such that a sample introduced into a sample introducing part of the porous carrier is allowed to move toward the determining part via the labelled part, wherein the porous carrier further comprises a bypass for the sample extending from the sample introducing part toward the determining part by passing through a periphery of the labelled part or by escaping the labelled part on the way.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

Figure 1:
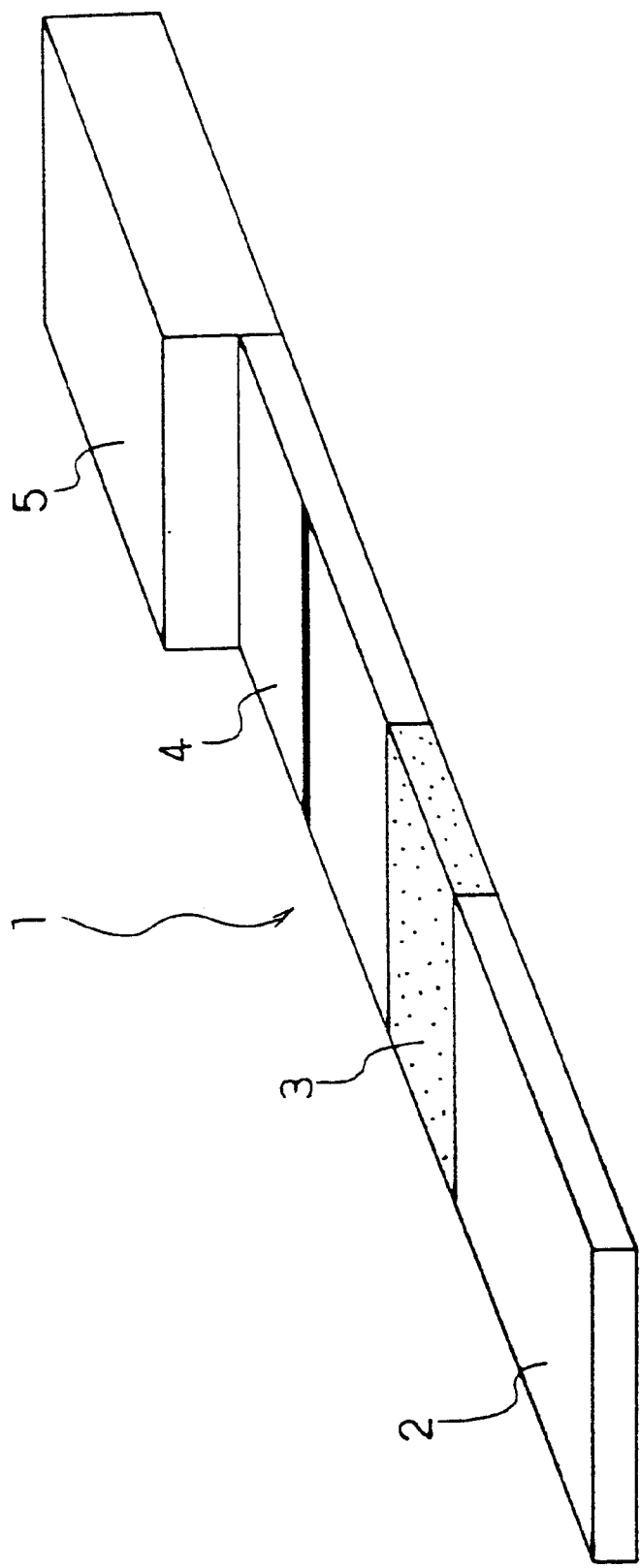
FIG. 1 is a perspective view illustrating a test strip of a conventional immunochromatography device.

The immunochromatography-assisted device in accordance with the present invention detects an antigen in an aqueous sample solution based on a specific antigen-antibody binding reaction, which comprises at least two different antibodies binding to an antigen as an analyte and a test strip composed of a porous carrier on which a labelled part containing one of the antibodies and a determining part containing the other of the antibodies are arranged such that a sample introduced into a sample introducing part is allowed to move toward the determining part via the labelled part, wherein one of the antibodies (the antibody in a mobile phase) is chemically visualized and contained in the labelled part of the porous carrier such that it dissolves in a sample solution introduced into the porous carrier in order to move inside the carrier with the movement of the sample solution, the other of the antibodies (the antibody in a fixed phase) is fixed to the determining part of the porous carrier to a degree not to be shifted in position by the movement of the sample, and the porous carrier has an impregnated part with an additive at a certain part between the sample introducing part and the determining part, the additive-impregnated part movably carrying thereon at least one selected from the group consisting of a surfactant, an ammonium salt and a pH buffer such that it dissolves in the sample solution and moves with the movement of the sample through the porous carrier.

The additive-impregnated part may be positioned between the sample introducing part and the labelled part or may be integrally combined with the sample introducing part.

If the additive-impregnated part is positioned between the sample introducing part and the determining part, the additive such as surfactant, ammonium ion of the ammonium salt or pH buffer is mixed with an introduced sample and moves toward the determining part in the course of analysis. The sample is absorbed in a fluid absorbing part after arriving at the determining part.

Of the various additives, the surfactant lowers the surface tension of a liquid sample to accelerate the flow of the sample, and modifies the surface characteristic of the antibody in the mobile phase to impair its hydrophobic bond with the porous carrier. This structure shortens the duration of detection with an immunochromatography-assisted device and inhibits coloring of the background to a minimum.

The ammonium ion, on the other hand, is a typical positive-charged compound, which effectively offsets the negative charge of the antibody in the mobile phase.

The pH buffer controls pH of the sample introduced, thereby offsetting the positive charge of the antibody in the fixed phase.

As such, these two additives can cancel electrical interaction between the mobile phase antibody and the fixed phase antibody, preventing the development of blank coloring.

In a preferred mode of the present invention, the labelled part is segmented into plural zones and a porous material for permitting movements of the sample and the labelled antibody is supplementarily positioned as a spacer between the plural zones of the labelled part such that the sample can flow through the segmented labelled part. The labelled part of this structure may carry different kinds and/or different absolute amounts of labelled antibody.

The labelled part may be segmented into plural zones such that plural zones of the segmented labelled part that are located proximal to the determining part, that is, those located downstream from the flow route carry the labelled antibody in a relatively large amount and plural zones that are located distal to the determining part, that is, those upstream from the flow route carry it in a small amount. This structure of the labelled part permits coexistence of a large amount of antigen in a sample with a large amount of labelled antibody in the labelled part downstream from the flow route if the sample contains a large amount of antigen. Thus, intense coloring can be induced in an acute phase of antigen-antibody reaction without developing a deficiency of the labelled antibody. If the sample contains only a small amount of antigen, the large amount of labelled antibody present downstream from the flow route fails to contribute to the antigen-antibody reaction; however, the antigen is condensed at the determining part and colored by the labelled antibody which later catches up with the antigen over time while flowing almost homogeneously. This means that this structure secures a high detectability of the device. In the latter case, since the labelled antibody which later catches up with the antigen has a low concentration, the background coloring remains diminished, causing no effect on the coloring of the determining part. According to this structure, an optimal reaction system participates in the antigen-antibody reaction, depending on the concentration of the antigen, which improves the dynamic range of detectability.

Division of the sample flow route into 2 routes is an effect produced by the bypass route extending from the sample introducing part toward the determining part such that the sample is allowed to partially pass the labelled part or to escape the labelled part to directly reach the determining part. One is a simple route that runs from the sample introducing part toward the determining part via the carrier. This route has minimal hindrances, and can pass the sample at a high rate. The alternative route passes through the labelled part, more preferably segmented labelled part, and develops contact-induced resistance on the interface between the labelled part and the spacer so as to delay the flow of the sample. In other words, according to this structure, upon introduction of a sample into the device, it occurs substantially that only the sample reaches the determining part and after a lapse of certain time the labelled antibody which has dissolved in the sample solution catches up with the sample to finally reach the determining part. During the delayed lapse of time, the determining part preliminarily accepts a mixture of the labelled antibody and the antigen in the sample such that the antigen is bound to the labelled antibody to a certain degree. Thus, the antigen can be captured efficiently even when the antigen in the sample is small in amount, resulting in improved detectability of the device. This structure appears to prolong the reaction time seemingly due to the presence of a delayed lapse of time. However, from the fact that the detectability of the device can be improved substantially without increasing an absolute amount of the labelled antibody carried on the labelled part, the time required for diminishing the background coloring can be reduced, which shortens the overall reaction time as a whole.

In another preferred mode of the present invention, the chemically visualized antibody, that is, mobile phase antibody is prepared by binding the antibody to any one of colloidal gold, latex particle, organic dye, pigment, metal, metallic oxide and enzyme or an arbitrary combination of a plurality of the above group to visualize the antibody. One example of preferred dyes is cyanine dye represented by the following chemical formula:

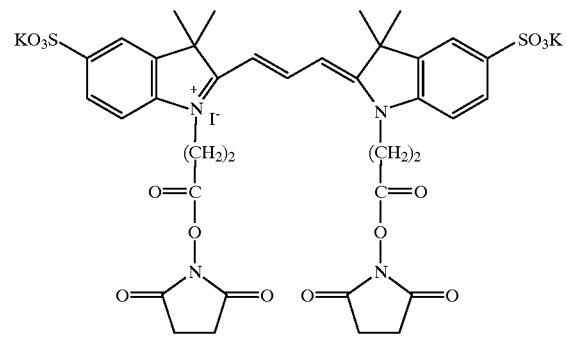

The immunochromatography-assisted device in accordance with the present invention is particularly effective if the antigen is either hCG, luteinizing hormone (LH) or C-reactive protein (CRP).

The surfactant for use in the present invention may be exemplified as non-ionic alkyl phenol ether surfactant. A Triton surfactant, particularly commercially available Triton X-100 is preferred.

Preferred ammonium salts include tetramethyl ammonium salts exemplified as tetramethyl ammonium chloride, tetramethyl ammonium bromide, tetramethyl ammonium iodide, etc.

It is preferable for the additive-impregnated part to carry a pH buffer in such an amount that makes a pH of 8.0 to 8.5 for a sample at the determining part when the sample is introduced into the sample introducing part of the carrier in a predetermined volume.

The pH buffer is preferably one selected from the group consisting of boric acid, 2-(N-morpholino)ethanesulfonic acid, tris(hydroxymethyl)aminomethane and phosphoric acid.

Figure 2:
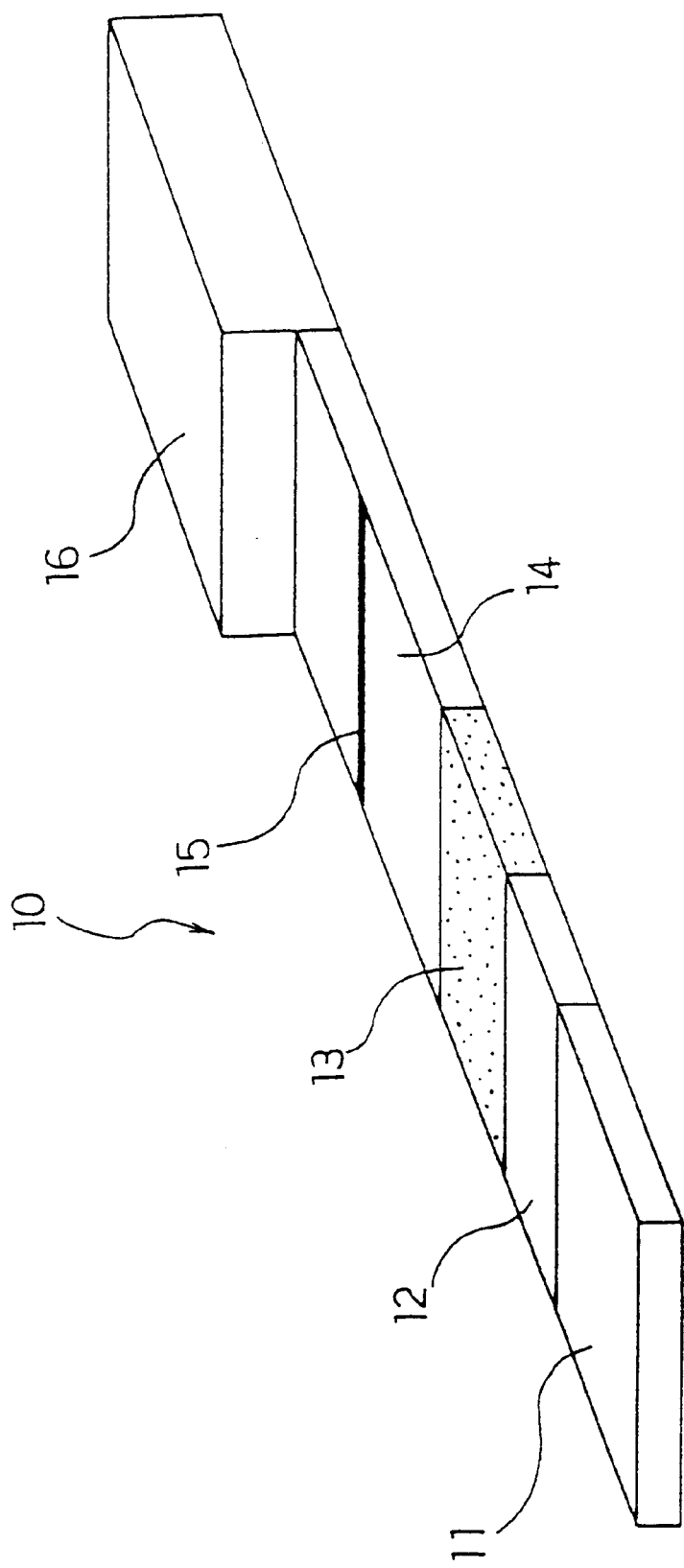
FIG. 2 is a perspective view illustrating the structure of a test strip for use in an immunochromatography-assisted device in accordance with the present invention.

FIG. 2 shows a structure of a test strip composed of a porous carrier for use in the immunochromatography-assisted device in accordance with the present invention. A test strip 10 composed of a porous carrier comprises a sample introducing part 11, an additive-impregnated part 12, a labelled part 13 containing a visualized mobile phase antibody, a determining part 14 having a fixed part 15 of a fixed phase antibody, and a fluid absorbing part 16 which are arranged successively on the porous carrier in this order.

The test strip 10 is accommodated in a hollow case made of a moisture-impervious material. The case has a window or fenestration for visually observing what happens at the determining part 14 on the carrier from the outside. In order to facilitate introduction of a sample into the sample introducing part 11 on the porous carrier from the outside, the hollow case is opened in part, or the porous carrier is extended in an opposite direction to the determining part by placing the labelled part in the center, so that the porous carrier can be exposed outside the hollow case to form a part of the sample introducing part.

Figure 3:
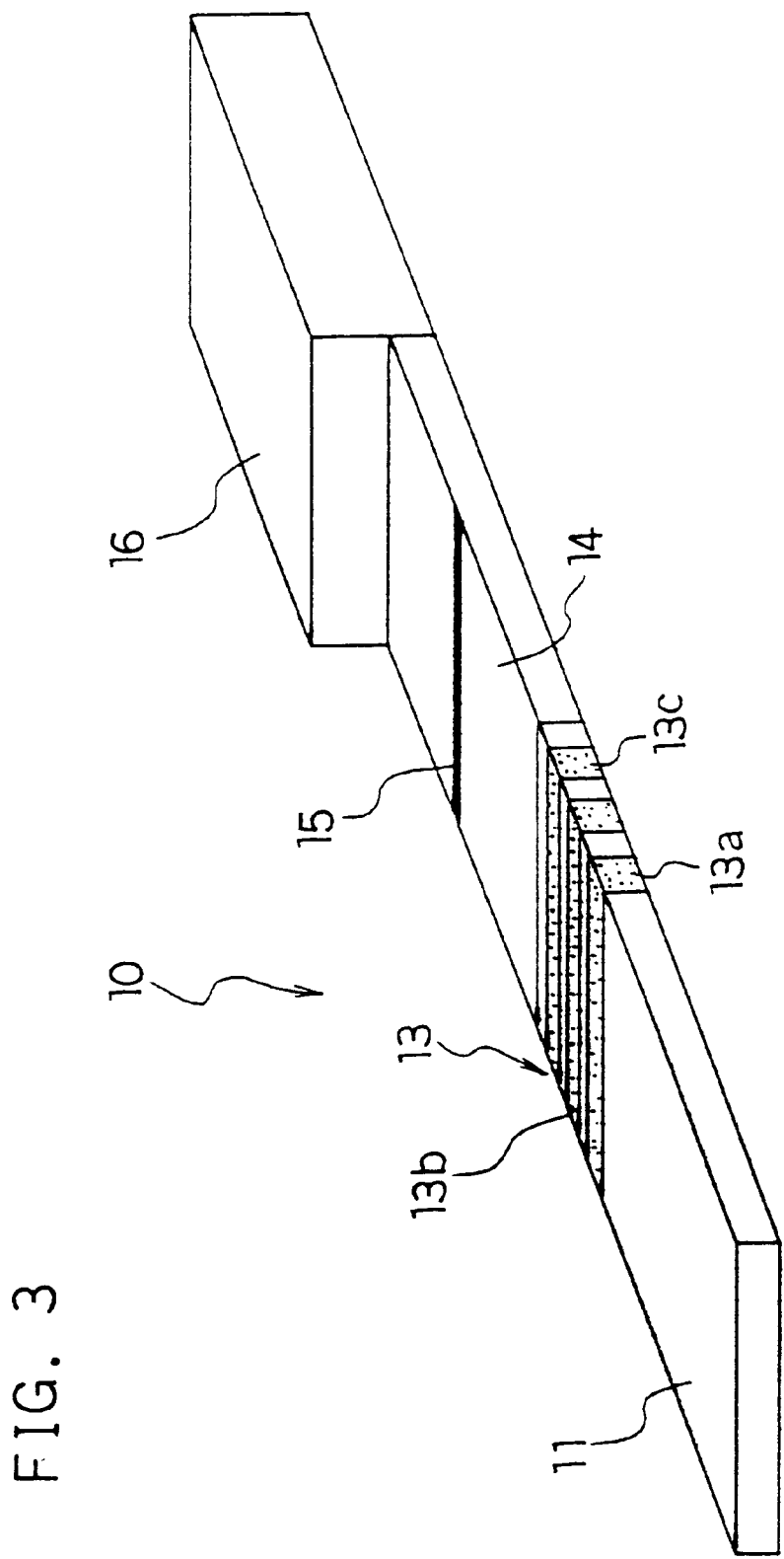
FIG. 3 is a perspective view illustrating another structure of the test strip for use in the immunochromatography-assisted device in accordance with the present invention.

FIG. 3 shows another preferred structure of the test strip. The labelled part 13 is divided into 13a, 13b and 13c. Although not shown, the additive-impregnated part is also formed on the porous carrier.

In the following, the present invention will be described specifically with reference to concrete examples.

EXAMPLE 1

I. Method of producing each part (1) Method of preparing a blocker and a detergent for the determining part To 1 L of distilled water, 0.1 mol (12.11 g) of tris (hydroxymethyl)aminomethane (hereinafter referred to as "Tris") was added and agitated, which was then adjusted for pH at 8.2 with 1 N HCl to make a detergent for nitrocellulose. Separately, 10 g of skimmed milk was added to the detergent thus prepared and agitated to make a blocker for nitrocellulose.

(2) Method of fixing the antibody at the determining part (Preparation of fixed phase antibody)

A nitrocellulose sheet (HFM SPHF04020, manufactured by Nihon Millipore Limited) was cut to a sheet of 0.9 cm×1.2 cm with a thickness of about 220 $\mu$m (including the thickness of a substrate) for use as a carrier. The sheet as the carrier was applied with a phosphate buffer solution (hereinafter abbreviated to "PBS") containing an anti-hCGβ antibody ($\alpha$-hCGβ) against hCG (5 mg/mL) at a portion 0.5 cm apart from the sample introducing part and 0.7 cm apart from the fluid absorbing part and dried for 8 hours at 40° C. in a light-tight environment. After drying, the sheet was impregnated with the above-mentioned blocker so as to make a ratio of the blocker at 70 mL per 30 sheets, and then shaken in a shaker for 30 min at 30° C. for blocking. After blocking, the sheet was rinsed with the above-mentioned detergent (70 mL/30 sheets) for 30 min at 30° C. three times, which was then placed and dried in a desiccator overnight.

(3) Method of producing the additive-impregnated part

To 1 L of distilled water, 1 mol (121.1 g) of Tris was added and agitated, which was then adjusted for pH at 8.2 with 1 N HCl. The mixture was further added with 1 mol (109.6 g) of tetramethylammonium chloride (hereinafter abbreviated to "TMA") and 10 mL of a 10% aqueous solution containing a Triton surfactant Triton X-100 (hereinafter referred to as "Triton") and agitated to make a Tris (1M)-TMA (1M)-Triton (0.1%) solution. The resultant solution was applied onto a 0.9 cm×6.0 cm sheet cut from a glass fiber filter (F075-14, manufactured by Whatman Japan Ltd.) at 0.36 mL, followed by freezing and drying.

(4) Method of producing the labelled part (a) A PBS of dithiobis(sulfosuccinimidylpropionate) (hereinafter abbreviated to "DTSSP")(4.06 mg/0.1 mL) was gently dropped on a PBS of anti-hCG$\alpha$ antibody ($\alpha$-hCG$\alpha$) (10 mg/mL) and agitated for 30 min at 35° C., which was then subjected to gel filtration using a molecular weight differential column (Sephadex G25M, manufactured by Amersham Pharmacia Biotech).

(b) Gel filtration produced a polymerized anti-hCG$\alpha$ antibody PBS (10 mg/6 mL). The solution thus produced was stored at 4° C. until use.

(c) A BSA PBS (110 mg/mL) was added with 77 mg of dithiothreitol (hereinafter abbreviated to "DTT") and agitated for 30 min at room temperature to make a final concentration of 7.7 mg/mL, which was then promptly subjected to gel filtration using a molecular weight differential column (Sephadex G25M, manufactured by Amersham Pharmacia Biotech). Gel filtration produced a BSA solution with a free SH group (totally 24 mL).

(d) The BSA with a free SH group (totally 24 mL) was mixed with the polymerized anti-hCG$\alpha$ antibody PBS (10 mg/6 mL) which had been stored at 4° C. after preparation in the above (b) and agitated for 20 hours at 4° C.

(e) In order to remove non-reacted BSA, the mixture prepared in the above (d) was subjected to gel filtration using a molecular weight differential column (Sephacryl S300HR, manufactured by Amersham Pharmacia Biotech). This gave a polymerized anti-hCG$\alpha$ antibody-BSA (totally 40 mL to 50 mL).

(f) The product of (e) was gently dropped with a PBS of a cyanine dye (hereinafter abbreviated to "SLIC3") represented by the chemical formula as shown above and then agitated for 20 hours at 4° C.

(g) In order to remove non-reacted cyanine dye, the mixture prepared in the above (f) was subjected to gel filtration using molecular weight differential columns of 50 cm and 150 cm (Sephadex G25M, manufactured by Amersham Pharmacia Biotech). This gave a polymerized anti-hCG$\alpha$ antibody-BSA-SLIC3 (totally 60 mL to 90 mL). This solution will be referred to as a stock solution of the labelled antibody.

(h) The stock solution thus obtained was added with BSA and sucrose at 1%, respectively, as stabilizers.

(i) A glass filter (F075-14, manufactured by Whatman Japan Ltd.) was cut to a sheet of 0.9 cm×5.0 cm and impregnated with the labelled antibody stock solution containing the two stabilizers at 0.3 mL per sheet, which was then frozen and dried.

(j) After freezing and drying, the sheet thus prepared was stored in a light-tight environment until use.

(5) Method of producing the fluid absorbing part

A glass fiber filter (GF/D, manufactured by Whatman Japan Ltd.) was cut to a sheet of 0.9 cm×2.5 cm and six (6) sheets were piled for use as the fluid absorbing part.

II. Method of producing the test strip

Figure 4:
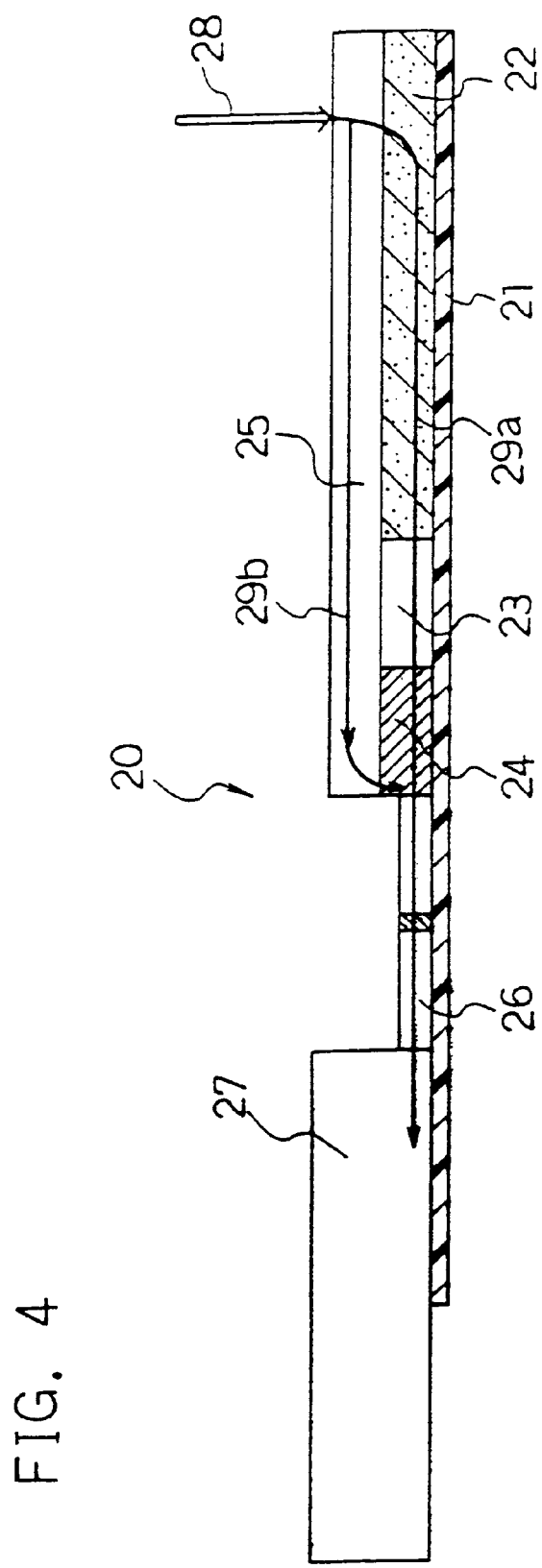
FIG. 4 is a vertical cross-sectional view showing a test strip for use in one example of the present invention.

FIG. 4 shows the structure of a test strip 20 in accordance with Example 1. The size of each constituent shown in FIG. 4 does not necessarily correspond to the real size.

On a surface of a lining 21 with a size of 0.9×5.5 cm and a thickness of 0.5 mm (hard polyvinyl chloride (white)) entirely and thoroughly lined with a double-sided adhesive tape of the same size (TW-12SD, manufactured by Nichiban Co., Ltd.), a determining part 26, a fluid absorbing part 27 downstream from the determining part 26 and a labelled part 24 upstream from the determining part 26 were bonded, respectively. Upstream from the labelled part 24, a sheet 23 of 0.9 cm×0.5 cm cut from a glass fiber sheet (F075-14, manufactured by Whatman Japan Ltd.) and an additive-impregnated part 22 were further bonded successively in this order. Two (2) additional sheets of the same glass fiber filter cut to a size of 0.9×3.5 cm were also bonded to the entire upper part from the labelled part 24 to the additive-impregnated part 22 to serve as a porous bypass 25. The test strip 20 thus produced was accommodated in a hollow case.

In the test strip 20, an end part of the additive-impregnated part 22 also serves as the sample introducing part. Upon introduction of a sample into the test strip as shown by an arrow 28 in FIG. 4, the sample flows through two routes. The major one is a flow route 29a which runs from the additive-impregnated part 22 toward the determining part 26 via the glass fiber filter 23 and the labelled part 24 on the course. The other is a flow route 29b which runs from the porous bypass 25 toward the determining part 26 by passing through a periphery of the labelled part 24 or by passing beyond the labelled part 24. In FIG. 4, the porous bypass 25 is shown to contact the labelled part 24 at its periphery, but it is more preferable for the porous bypass 25 to directly contact the determining part 26 beyond the labelled part 24.

If the test strip is formed in this way, the flow route 29b that runs toward the determining part 26 by passing through a periphery of the labelled part 24 or by passing beyond the labelled part 24 is less in hindrance and allows the sample to flow faster than the flow route 29a that passes through all the parts before reaching the final destination. The flow route 29a is a route which delays the flow of the sample. Therefore, if a sample is introduced, a part of the sample which is almost free of the labelled antibody in the labelled part 24 arrives at the determining part 26 primarily and after a lapse of certain time, the labelled antibody which has dissolved in the sample will catch up with the sample to arrive at the determining part. During the delayed lapse of time, the determining part preliminarily accepts a mixture of the labelled antibody and the antigen in the sample such that the antigen is bound to the labelled antibody to a certain degree. Thus, the antigen can be captured efficiently even when the antigen in the sample is small in amount.

As stated previously, this structure increases the viewability and improves detectability of the device. Although the presence of a delayed time appears to prolong the reaction time seemingly, the detectability of the device can be improved actually without increasing the absolute amount of the labelled antibody carried on the labelled part, which shortens the time required for diminishing background coloring and therefore shortens the reaction time as a whole.

COMPARATIVE EXAMPLE 1

For comparison, a test strip as shown in FIG. 4 was prepared in the same manner as in Example 1, except for the use of the same glass fiber filter as used in the glass fiber filter 23 in place of the additive-impregnated part 22 and an omission of the porous bypass 25 of a glass fiber filter.

Two immunochromatography-assisted devices were produced using the test strip prepared in Example 1 and the one prepared in Comparative Example 1, respectively, and tested for detectability, reaction time and viewability. The analyte is hCG. The range of hCG concentrations for measurement to determine the detectability was 100,000 IU/L to 0 IU/L and the amount of hCG solution as a sample to be introduced into the sample introducing part was 0.45 mL. The reaction time was defined as a time lapse from the introduction of hCG solution into the sample introducing part until visualization of a line of the fixed part of the fixed antibody by a reaction between the fixed anti-hCGβ antibody and the labelled anti-hCGα antibody via hCG as the antigen. The numerical value of viewability was derived from the measurement results with a reflective spectrophotometer (CS-9300, manufactured by Shimadzu Corporation). The intensity of reflected light was measured at an incident light of 550 nm (absorbance of SLIC3). The baseline value 0 was based on the absorbance of clean nitrocellulose. The time of measurement of the absorbance was within 30 minutes after termination of immunochromatographic analysis.

Figure 5:
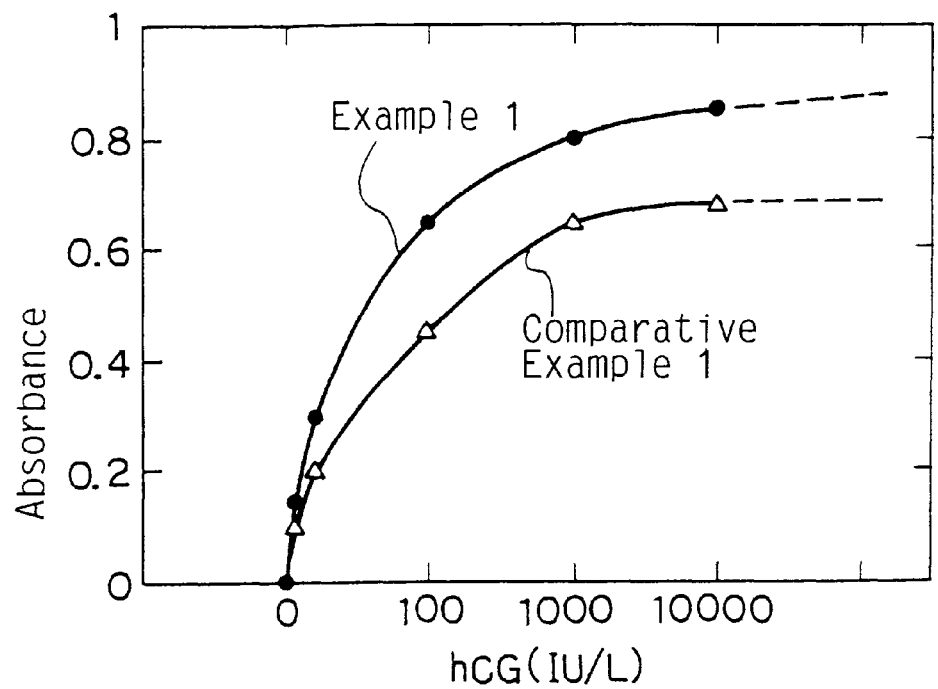
FIG. 5 is a graph illustrating the relationship between the concentration of hCG in a sample and the absorbance (coloring intensity) at the determining part.
Figure 6:
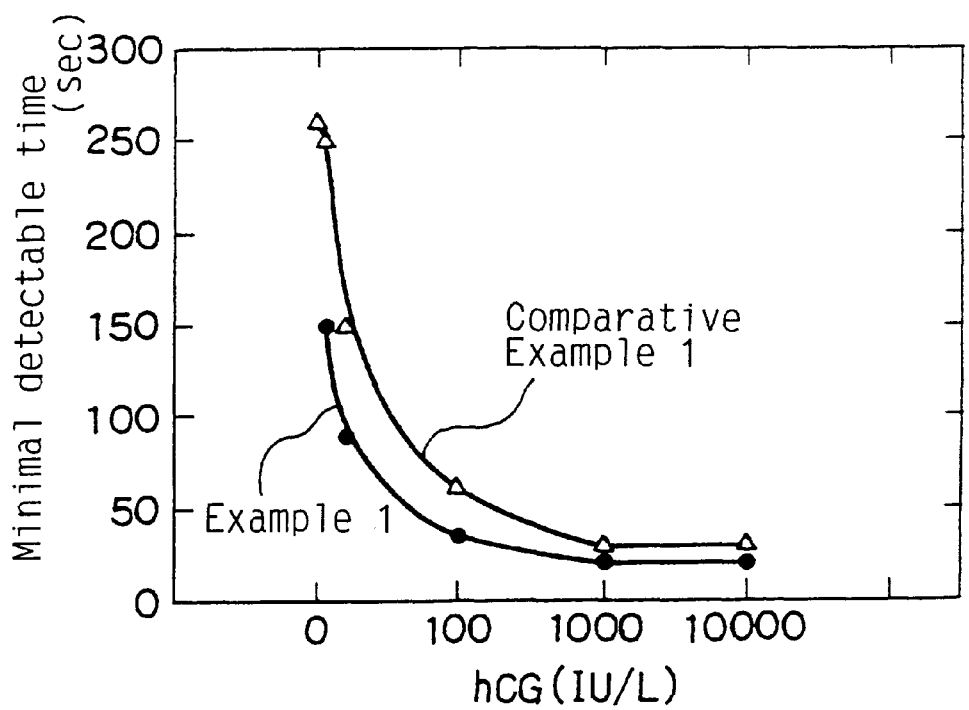
FIG. 6 is a graph illustrating the relationship between the concentration of hCG in a sample and the minimal detectable time.
Figure 7:
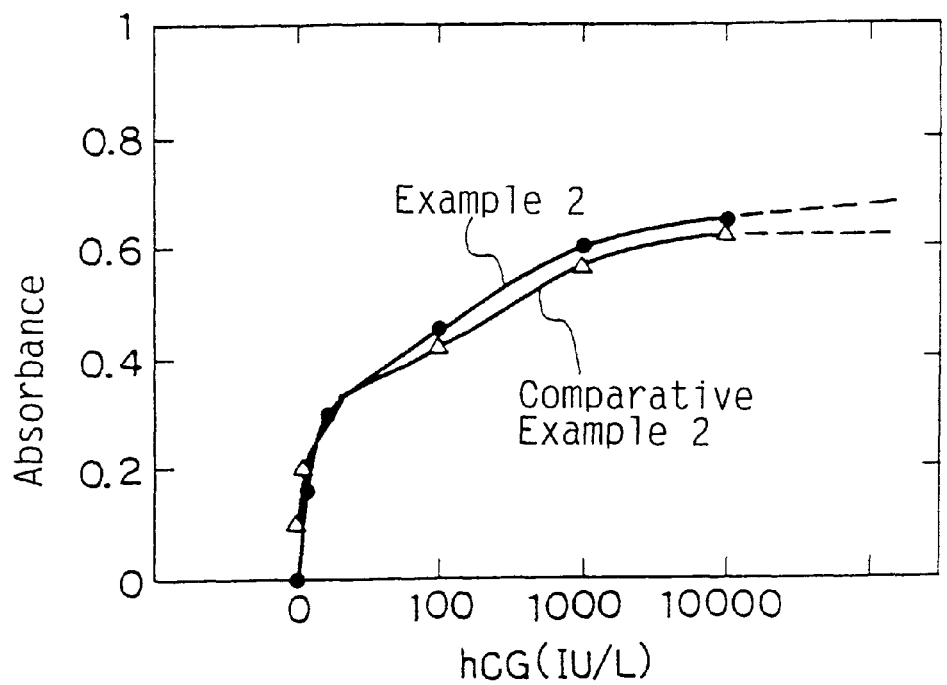
FIG. 7 is another graph illustrating the relationship between the concentration of hCG in a sample and the absorbance at the determining part.
Figure 8:
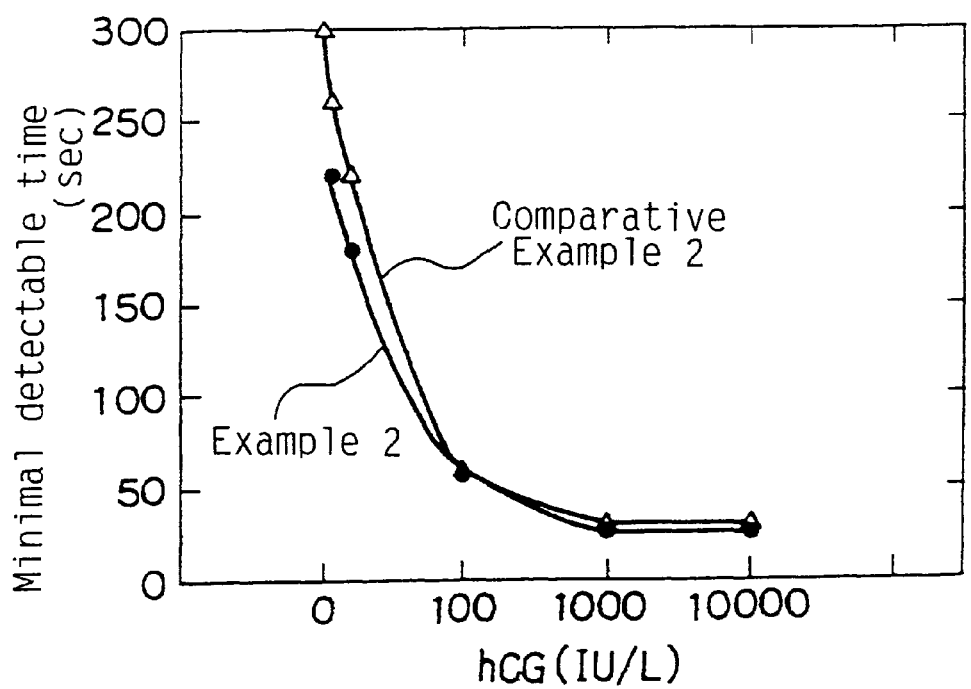
FIG. 8 is another graph illustrating the relationship between the concentration of hCG in a sample and the minimal detectable time.
Figure 9:
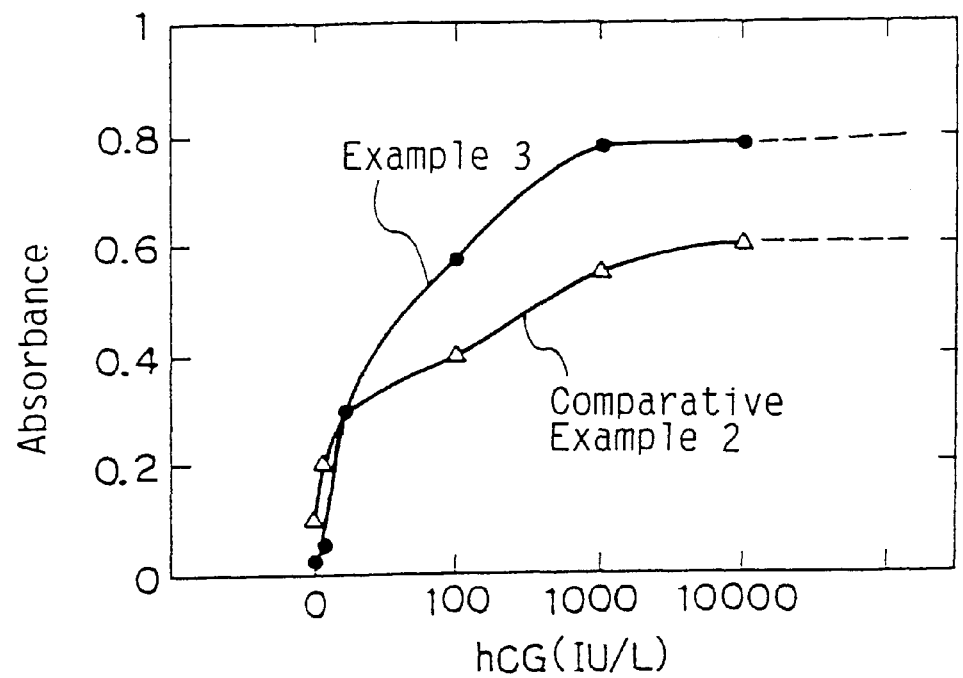
FIG. 9 is still another graph illustrating the relationship between the concentration of hCG in a sample and the absorbance at the determining part.
Figure 10:
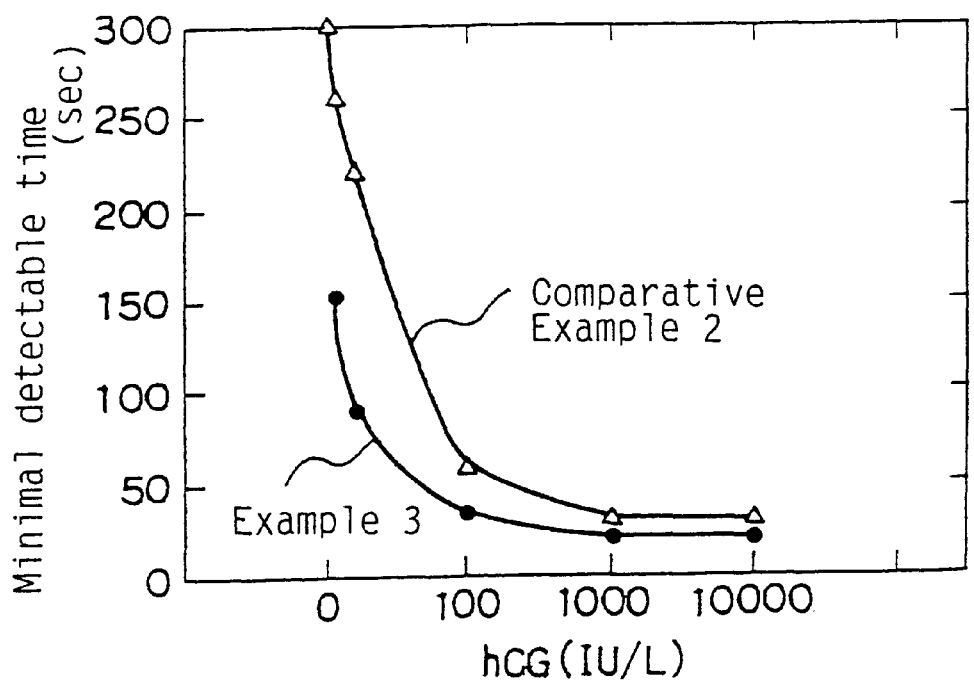
FIG. 10 is still another graph illustrating the relationship between the concentration of hCG in a sample and the minimal detectable time.

FIG. 5 shows a comparison of the viewability between the two devices based on the intensity of absorbance as defined above and FIG. 6 shows a comparison of the detectable minimal time. Although not shown in the figures, the absorbance peaked at 0.5 as late as 30 seconds after introduction of the sample for the device of Comparative Example 1, and 0.7 as early as 20 seconds after introduction of the sample for the device of Example 1 when the concentration of hCG was 10,000 IU/L. These results indicate that the immunochromatography-assisted device in accordance with the present invention is superior to the conventional device of Comparative Example 1 in detectability, reaction time and viewability.

EXAMPLE 2

In this example, a test strip was prepared in the same manner as in Example 1, except for the use of Tris (1M)-TMA (1M) solution in place of Tris (1M)-TMA (1M)-Triton (0.1%) solution in Example 1 in producing the additive-impregnated part.

EXAMPLE 3

In this example, another test strip was prepared in the same manner as in Example 1, except for the use of Tris (1M)-Triton (0.1%) solution in place of Tris (1M)-TMA (1M)-Triton (0.1%) solution in Example 1 in producing the additive-impregnated part.

COMPARATIVE EXAMPLE 2

For comparison, a test strip was prepared in the same manner as in Example 2, except for the use of the same glass fiber filter as used in the glass fiber filter 23 in place of the additive-impregnated part 22 in Example 2.

Three immunochromatography-assisted devices were produced using the test pieces prepared in Examples 2 and 3 and Comparative Example 2, respectively, and tested in the same manner as in Example 1. The results are shown in FIG. 7 to FIG. 10.

Figure 11:
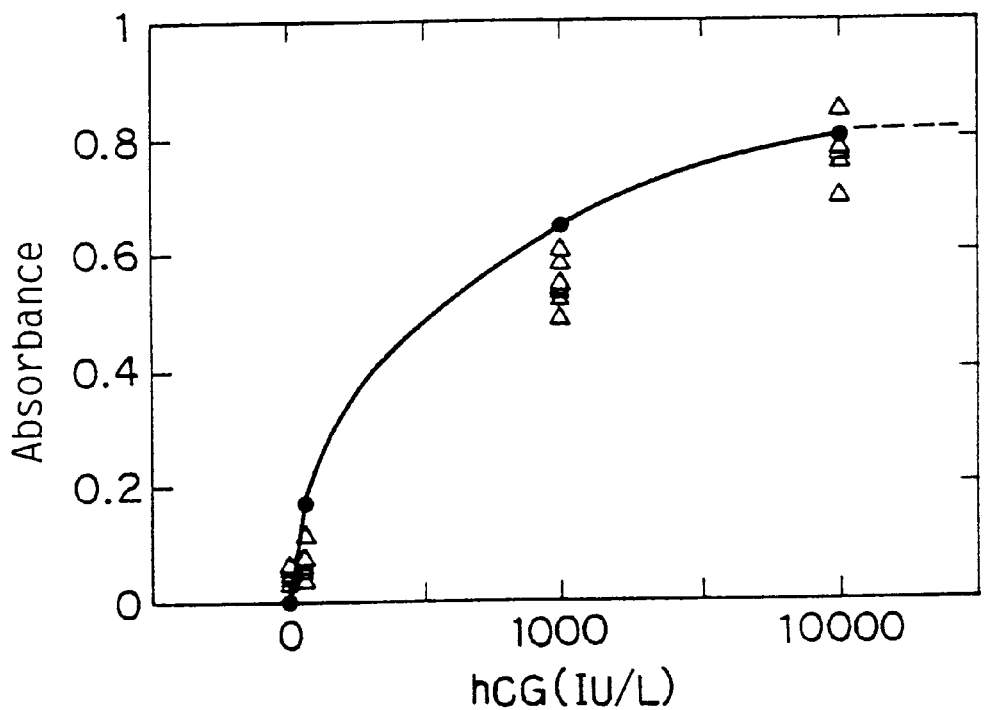
FIG. 11 is a graph illustrating the relationship between the concentration of hCG in a sample and the absorbance at the determining part obtained by varying the pH of a sample solution carried on the test strip.

Other test pieces were prepared in the same manner as in Example 1, except for the use of Tris solutions at various pH's in place of Tris (1M)-TMA (1M)-Triton (0.1%) solution in Example 1 in producing the additive-impregnated part. This is to make the sample have various pH's when they are introduced into the test strip in a predetermined amount. FIG. 11 shows the relationship between the pH of the sample at analysis and the absorbance.

As stated previously, the cause of blank coloring (0 IU/L) is electrical binding between the antibody labelled with a dye having negative charge and the fixed phase antibody having positive charge. Therefore, if the sample solution to be tested on the test strip has an adjusted pH of 8.2, the positive charge of the fixed phase antibody can be cancelled. When TMA with positive charge was further added to the test strip, the negative charge of the dye for labelling the antibody could be cancelled, resulting in successful removal of blank coloring (cf. FIG. 7). Further addition of a surfactant shortened the time periods until coloring and detection (cf. FIG. 10).

EXAMPLE 4

A test strip was prepared in the same manner as in Example 1, except that the labelled part was produced in the manner as described below.

Method of preparing the labelled part

After the procedures a) to j) shown in Example 1, additional treatments k) and l) as shown below were performed.

k) The frozen and dried glass filter impregnated with the labelled antibody was cut to a size of 0.9 cm×0.1 cm and used as a labelled part 24c.

l) The stock solution of the labelled antibody was diluted 4-fold with PBS and impregnated into a glass fiber filter (F075-14, manufactured by Whatman Japan Ltd.) in the same manner as described previously, which was cut into two sheets of 0.9 cm×0.1 cm and used as labelled parts 24a and 24b.

Figure 12:
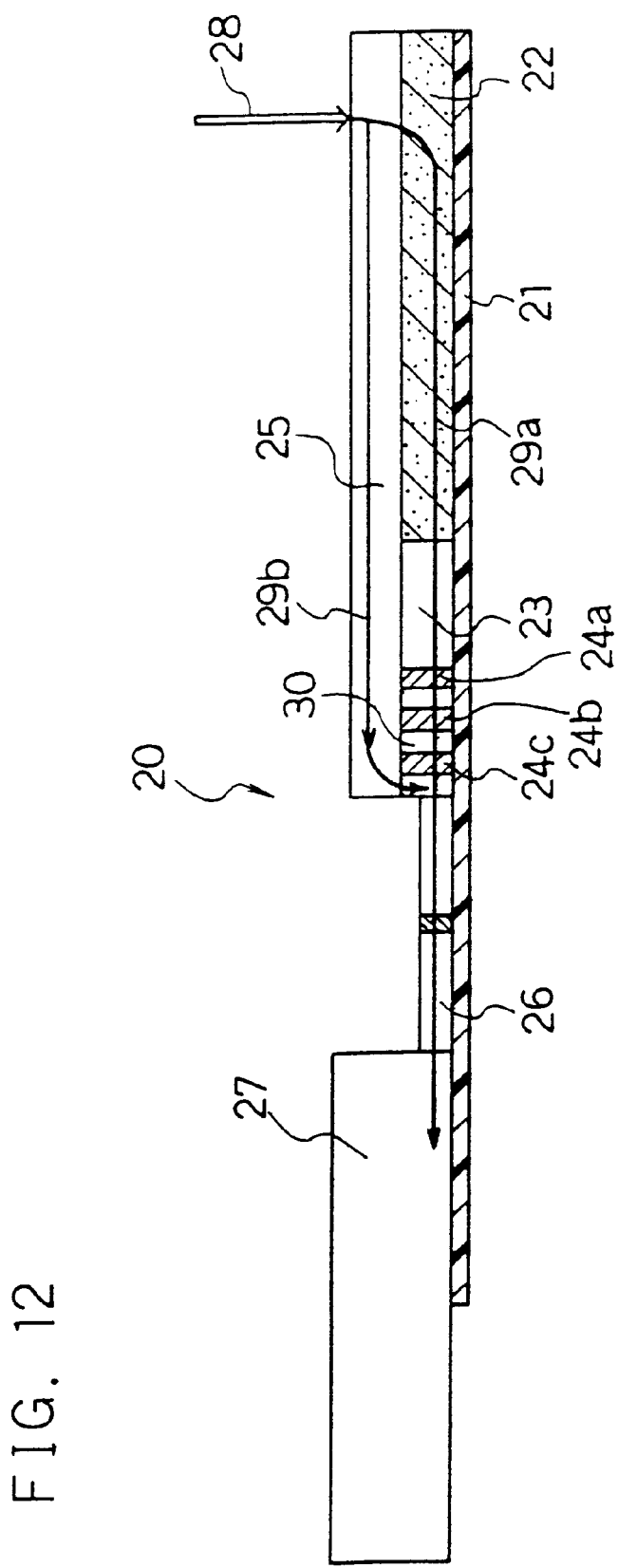
FIG. 12 is a vertical cross-sectional view illustrating a test strip for use in another example of the present invention.

The labelled parts 24a, 24b and 24c thus prepared were assembled and bonded to the porous carrier as shown in FIG. 12 by sandwiching therebetween spacers 30 made of a glass fiber filter (F075-14, manufactured by Whatman Japan Ltd.) of the same size.

EXAMPLE 5

Figure 13:
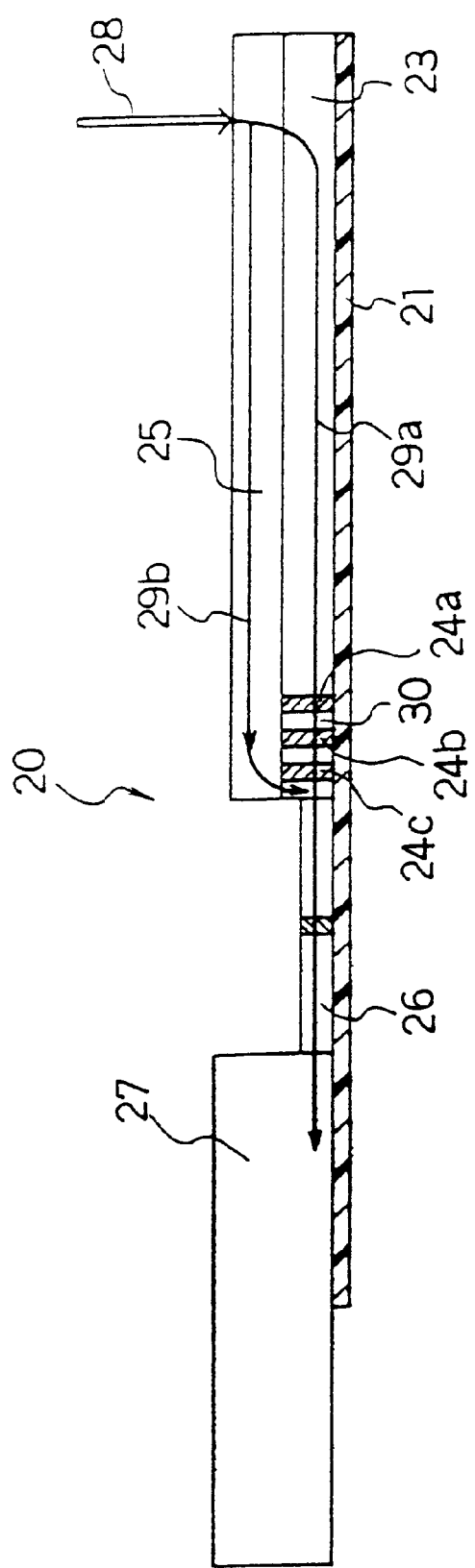
FIG. 13 is a vertical cross-sectional view illustrating a test strip for use in a further example of the present invention.

A test strip was prepared in the same manner as in Example 4, except for the use of a glass fiber filter (F075-14, manufactured by Whatman Japan Ltd.) in place of the additive-impregnated part 22 of Example 4 as shown in FIG. 13.

In the following, the results of a comparative experiment for verification of the effect of the segmented labelled part will be described.

In the experiment, an immunochromatography-assisted device was produced using the test strip prepared in Example 5 in accordance with the present invention and compared with an immunochromatography-assisted device of a comparative example produced with a test strip similar to that of Example 5, except that the labelled part was not segmented, and the part facing the determining part was positioned at the same place as the labelled part 24c of Example 5 for comparison purpose. This mean that both devices are the same in terms of the total amount of the labelled antibody carried on the labelled part. The analyte was hCG. Reaction-induced coloring was assayed using a reflectance spectrophotometer (CS-9300, manufactured by Shimadzu Corporation). The intensity of reflected light was measured at an incident light of 550 nm (absorbance of SLIC3). The baseline value 0 was based on the absorbance of clean and non-used nitrocellulose. hCG PBS at a concentration of 0, 50, 1,000, or 10,000 IU/L was introduced into the sample introducing part of the test strip of each device. After the device was stood still horizontally at room temperature (25° C.), the reaction was analyzed.

Figure 14:
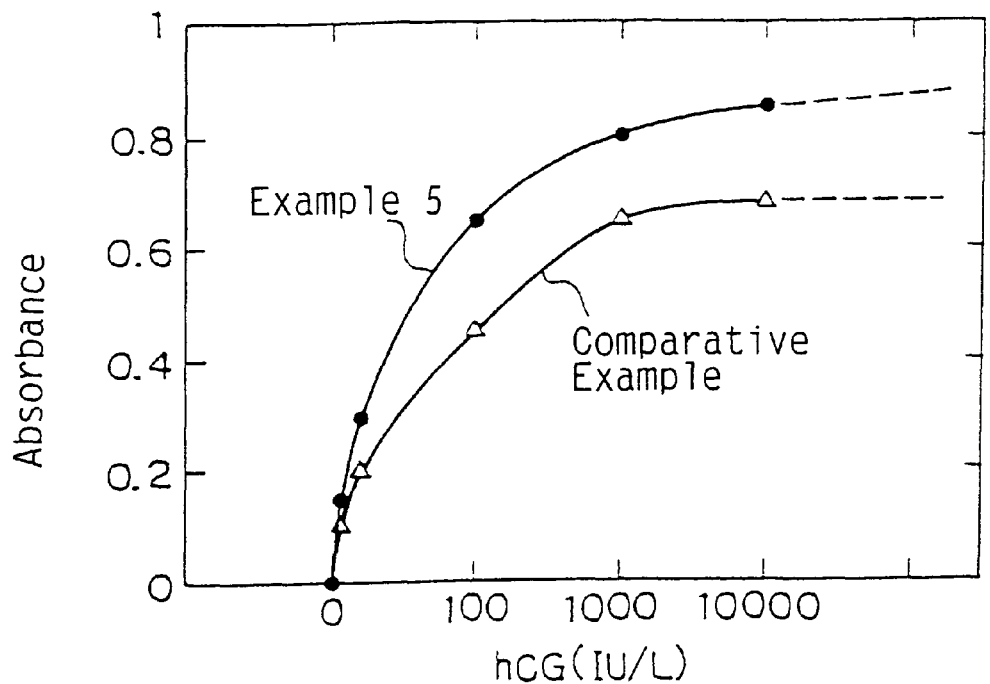
FIG. 14 is a graph illustrating the relationship between the concentration of hCG in a sample and the absorbance at the determining part.
Figure 15:
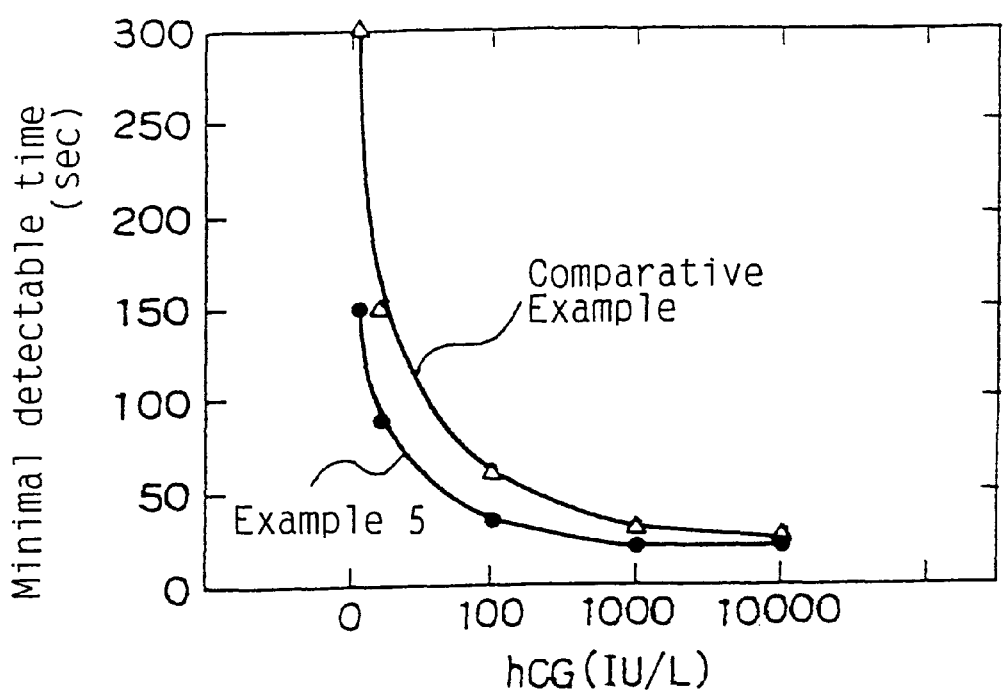
FIG. 15 is a graph illustrating the relationship between the concentration of hCG in a sample and the minimal detectable time.

FIG. 14 summarizes the results of measurement of absorbance for the respective hCG PBS at various concentrations 3 minutes after introduction of the sample. FIG. 15 plots the time point from sample introduction until the time point when the difference between the determined absorbance and the background absorbance became 0.2. As shown in FIG. 14, the device in accordance with the present invention shows intense coloring at all hCG concentrations. Particularly at a high hCG concentration of 10,000 IU/L, the device of the comparative example developed a malfunction of reduced coloring, but the device of the present invention demonstrated normal coloring. This finding indicates enhanced detectability and improved dynamic range for the latter. As is evident from FIG. 15, coloring time (reaction time) is promoted at all hCG concentrations for the device of the present invention, compared to the device of the comparative example. Although not shown in the figures, at the high hCG concentration of 10,000 IU/L, the device of the present invention had a peak absorbance of 0.7 as early as 20 seconds after sample introduction, whereas the device of the comparative example had a peak absorbance of only 0.5 as late as after 30 seconds.

Figure 16:
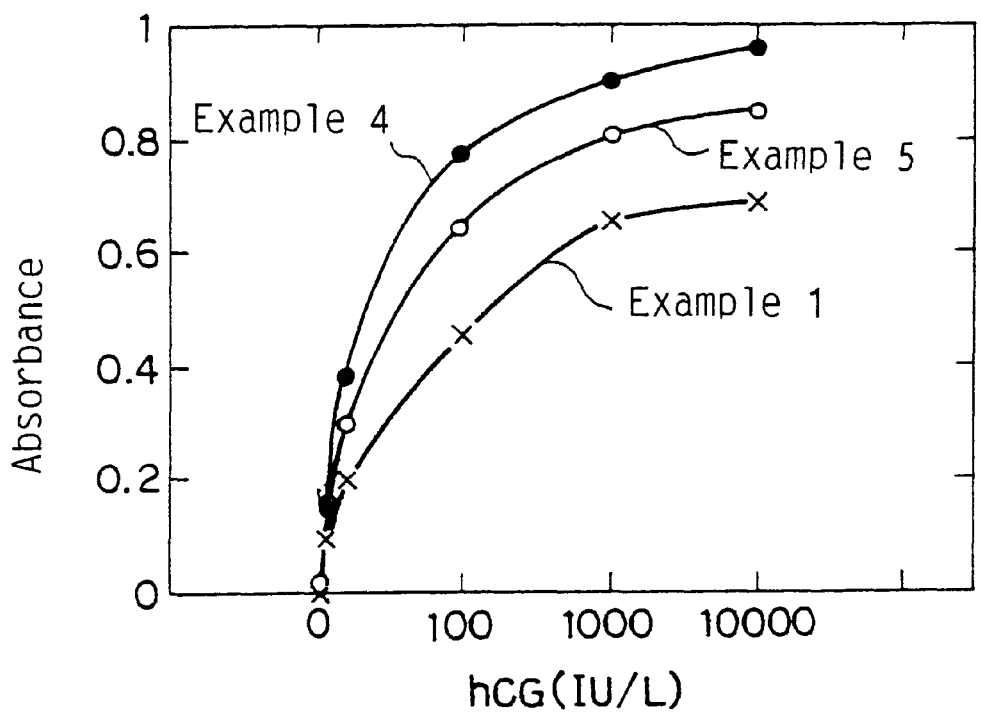
FIG. 16 is another graph illustrating the relationship between the concentration of hCG in a sample and the absorbance at the determining part.

Next, the results of a comparison test between three (3) immunochromatography-assisted devices using the test strip of Example 1, Example 4 or Example 5. The analyte was hCG. As stated previously, the viewability was derived from the measurement of the intensity of reflected light at an incident light of 550 nm. hCG PBS at a concentration of 0, 50, 100, 1,000, or 10,000 IU/L was introduced into the sample introducing part of the test strip of each device and the device was stood still horizontally at room temperature (25° C.). FIG. 16 summarizes a comparison between the devices for the absorbance (coloring intensity) at each hCG concentration 3 minutes after sample introduction. The figure indicates that the device using the test strip of Example 4 which includes an additive and is segmented for the labelled part is improved in coloring intensity, compared to the devices using the test strip of Example 1 or Example 5 from which either one has been omitted. Blank coloring at 0 IU/L as a factor for causing a malfunction could be eliminated perfectly from Example 4.

As discussed above, the present invention can perfectly eliminate background and blank coloring which may cause a malfunction at detection. Therefore, use of the immunochromatography-assisted device in accordance with the present invention facilitates accurate and rapid detection of an antigen contained in liquid samples of any kind. The present invention permits a labelled antibody to play a role in antigen-antibody reaction in its best condition. As a result, detection speed, detectability and dynamic range of detection can be realized at the same time.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. An immunochromotography-assisted device for detecting an antigen in an aqueous sample solution based on a specific antigen-antibody binding reaction, said device comprising:

at least two different antibodies capable of binding to an antigen and a test strip composed of a porous carrier which has a labelled part segmented into plural zones containing one of said antibodies and a determining part containing the other of said antibodies, said labelled part and said determining part being arranged such that a sample introduced into a sample introducing part is allowed to move toward said determining part via said labelled part, wherein one of said antibodies is a labelled antibody and contained in said labelled part of said porous carrier such that it dissolves in a sample solution introduced into said porous carrier in order to move inside the carrier with the movement of said sample;

the other of said antibodies is fixed to said determining part of said carrier to a degree not to be shifted in position by the movement of the sample; and said porous carrier has an impregnated part with an additive at a certain part between said sample introducing part and said determining part, said impregnated part movably carrying thereon at least one additive selected from the group consisting of a surfactant, an ammonium salt and a pH buffer such that it dissolves in said sample solution in order to move with the movement of said sample through said porous carrier.

2. The immunochromatography-assisted device in accordance with claim 1, wherein said labelled antibody is bound to at least one label selected from the group consisting of colloidal gold, latex particle, organic dye, pigment, metal, metallic oxide and enzyme.

3. The immunochromatography-assisted device in accordance with claim 1, wherein said labelled antibody is labelled with a cyanine dye represented by the following formula:

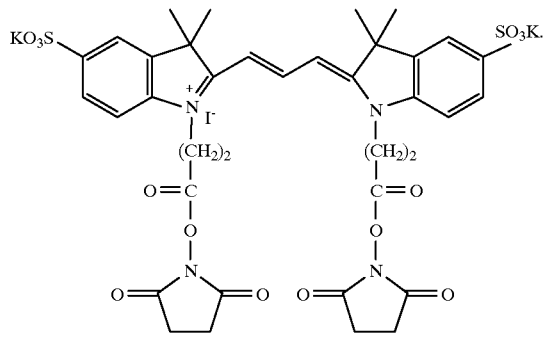

4. The immunochromatography-assisted device in accordance with claim 1, wherein said surfactant is a non-ionic alkyl phenol ether surfactant.

5. The immunochromatography-assisted device in accordance with claim 1, wherein said ammonium salt is a tetramethyl ammonium salt.

6. The immunochromatography-assisted device in accordance with claim 1, wherein said impregnated part carries said pH buffer in such an amount that allows said sample to have a pH of 8.0 to 8.5 at said determining part when said sample is introduced into said sample introducing part of said carrier in a predetermined amount.

7. The immunochromatography-assisted device in accordance with claim 1, wherein said pH buffer is at least one selected from the group consisting of boric acid, 2-(N-morpholino)ethanesulfonic acid, tris(hydroxymethyl)aminomethane and phosphoric acid.

8. The immunochromatography-assisted device in accordance with claim 1, wherein one zone of said segmented labelled part carries said labelled antibody in a different amount from those in other zones.

9. The immunochromatography-assisted device in accordance with claim 8, wherein plural zones of said segmented labelled part that are located proximal to said determining part carry said labelled antibody in a larger amount than plural zones that are located distal to said determining part.

10. The immunochromatography-assisted device in accordance with claim 1, further comprising a flow route allowing direct approach of said sample to said determining part either by only partially passing or by completely escaping said labelled part, in addition to a flow route allowing in-series passage of said sample through plural zone of said labelled part before reaching said determining part.

11. The immunochromatography-assisted device in accordance with claim 1, wherein a porous material permitting movements of said sample and said labelled antibody is positioned between said plural zones of said labelled part.

12. The immunochromatography-assisted device in accordance with claim 1, further comprising a bypass for said sample extending from said sample introducing part toward said determining part by passing through a periphery of said labelled part or by escaping said labelled part.

13. The immunochromatography-assisted device in accordance with claim 1, wherein the aqueous sample solution flows at different rates along two flow routes simultaneously.

14. The immunochromotography-assisted device in accordance with claim 1, wherein the additive functions to inhibit or prevent coloring of a background or development of blank coloring.

15. An immunochromatography-assisted device for detecting an antigen in an aqueous sample solution based on a specific antigen-antibody binding reaction, said device comprising:

at least two different antibodies binding to an antigen and a test strip composed of a porous carrier which has a labelled part containing one of said antibodies and a determining part containing the other of said antibodies, said labelled part and said determining part being arranged such that a sample introduced into a sample introducing part is allowed to move toward said determining part via said labelled part, wherein one of said antibodies is a labelled antibody and contained in said labelled part of said porous carrier such that it dissolves in a sample solution introduced into said porous carrier in order to move inside the carrier with the movement of said sample;

the other of said antibodies is fixed to said determining part of said carrier to a degree not to be shifted in position by the movement of the sample; and said labelled part is segmented into plural zones.

16. An immunochromatography-assisted device for detecting an antigen in an aqueous sample solution based on a specific antigen-antibody binding reaction, said device comprising:

at least two different antibodies binding to an antigen and a test strip composed of a porous carrier which has a labelled part containing one of said antibodies and a determining part containing the other of said antibodies, said labelled part and said determining part being arranged such that a sample introduced into a sample introducing part is allowed to move toward said determining part via said labelled part, wherein one of said antibodies is a labelled antibody and contained in said labelled part of said porous carrier such that it dissolves in a sample solution introduced into said porous carrier in order to move inside the carrier with the movement of said sample;

the other of said antibodies is fixed to said determining part of said carrier to a degree not to be shifted in position by the movement of the sample; and said porous carrier has a bypass for said sample extending from said sample introducing part toward said determining part by passing through a periphery of said labelled part or by escaping said labelled part.

17. The immunochromatography-assisted device in accordance with claim 16, wherein the aqueous sample solution flows at different rates along two flow routes simultaneously.

* * * * *